United States Patent
Kurth et al.

(10) Patent No.: US 11,795,327 B2
(45) Date of Patent: Oct. 24, 2023

(54) FLEXIBLE WAX AND METHOD OF MAKING SAME

(71) Applicant: CARGILL, INCORPORATED, Wayzata, MN (US)

(72) Inventors: Todd L. Kurth, Maple Grove, MN (US); Mariah Elizabeth Lindahl, Maple Grove, MN (US); Timothy Alan Murphy, Albertville, MN (US); Christopher Patrick Stevermer, St. Louis Park, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 320 days.

(21) Appl. No.: 16/961,740

(22) PCT Filed: Jan. 14, 2019

(86) PCT No.: PCT/US2019/013473
§ 371 (c)(1),
(2) Date: Jul. 13, 2020

(87) PCT Pub. No.: WO2019/140375
PCT Pub. Date: Jul. 18, 2019

(65) Prior Publication Data
US 2021/0062003 A1 Mar. 4, 2021

Related U.S. Application Data

(60) Provisional application No. 62/617,378, filed on Jan. 15, 2018.

(51) Int. Cl.
*C08L 91/06* (2006.01)
*A23L 33/12* (2016.01)
*A61K 8/92* (2006.01)
*C09D 191/06* (2006.01)
*C12P 7/6436* (2022.01)
*A61Q 19/00* (2006.01)
(Continued)

(52) U.S. Cl.
CPC ............... *C08L 91/06* (2013.01); *A23L 33/12* (2016.08); *A61K 8/92* (2013.01); *A61Q 19/00* (2013.01);
(Continued)

(58) Field of Classification Search
CPC ...... C08L 91/06; C08L 2201/06; C08L 91/02; A23L 33/12; A61K 8/92; A61K 2800/10;
(Continued)

(56) References Cited

U.S. PATENT DOCUMENTS

| 4,292,088 A | 9/1981 | Scheuffgen |
| 8,758,597 B2 | 6/2014 | Osborn |

(Continued)

FOREIGN PATENT DOCUMENTS

| CN | 101205369 A | 6/2008 |
| JP | 2002275020 A | 9/2002 |

(Continued)

*Primary Examiner* — Deborah D Carr

(57) ABSTRACT

The disclosure relates to flexible wax compositions and a method of making the same. Described herein is a wax composition containing about 20 wt % to about 45 wt % monoacylglycerides, about 28 wt % to about 40 wt % diacylglycerides, and about 10 wt % to about 45 wt % acylglyceride polymers, which contain one or more dimerized fatty acid residue and a plurality of glycerol moieties. The flexible wax composition described herein has an average creep stiffness of less than about 30 MPa and can be used in candles, paper coatings, box coatings, fruit coatings, broadsizing for OSB, tire and rubber, polyvinyl chloride piping, crayons, and personal care applications.

19 Claims, 2 Drawing Sheets

(51) Int. Cl.
  *B60C 1/00* (2006.01)
  *C11C 1/04* (2006.01)
  *C11C 3/02* (2006.01)
  *C11C 3/10* (2006.01)
  *C11C 5/00* (2006.01)

(52) U.S. Cl.
  CPC .............. *B60C 1/00* (2013.01); *C09D 191/06* (2013.01); *C11C 1/045* (2013.01); *C11C 3/02* (2013.01); *C11C 3/10* (2013.01); *C11C 5/002* (2013.01); *C12P 7/6436* (2013.01); *A23V 2002/00* (2013.01); *A61K 2800/10* (2013.01); *C08L 2201/06* (2013.01)

(58) Field of Classification Search
  CPC ........ A61Q 19/00; B60C 1/00; C09D 191/06; C11C 1/045; C11C 3/02; C11C 3/10; C11C 5/002; C11C 5/02; C12P 7/6436; A23V 2002/00
  See application file for complete search history.

(56) References Cited

U.S. PATENT DOCUMENTS

| | | |
|---|---|---|
| 2008/0145808 A1 | 6/2008 | Lee |
| 2009/0217568 A1 | 9/2009 | Murphy |
| 2011/0277661 A1* | 11/2011 | Murphy ................. C09D 13/00 264/237 |
| 2014/0076777 A1 | 3/2014 | Kriz |
| 2014/0144069 A1* | 5/2014 | Murphy ................. C11C 5/002 44/275 |

FOREIGN PATENT DOCUMENTS

| | | |
|---|---|---|
| JP | 2005089487 A | 4/2005 |
| JP | 2007284371 A | 11/2007 |
| JP | 2017197701 A | 11/2017 |
| WO | 2006076364 A2 | 7/2006 |
| WO | 2014058872 A1 | 4/2014 |
| WO | WO-2014058872 A1 * | 4/2014 ........... C07C 29/132 |

* cited by examiner

FLEXIBLE WAX AND METHOD OF MAKING SAME

CROSS-REFERENCE TO RELATED APPLICATIONS

This application claims the benefit of priority to U.S. Provisional Application Ser. No. 62/617,378, filed Jan. 15, 2018, which is incorporated by reference herein in its entirety.

TECHNICAL FIELD

This application relates to natural oil-based wax compositions and methods of making the same.

BACKGROUND

Beeswax is a naturally occurring wax which has been used since prehistoric times. Although beeswax has remained useful in the modern era, it has become increasingly costly and scarce. The advent of paraffin wax in the 19$^{th}$ century, in parallel with the development of petroleum refining, provided a bountiful and low-cost alternative to beeswax. Today, paraffin is the primary industrial wax used to produce candles and other wax-based products.

Conventional candles produced from a paraffin typically emit smoke, particles and odor when burning. A candle that has a reduced amount of paraffin or no paraffin at all would be preferable. Modern candle-makers have become increasingly sophisticated and seek materials which improve manufacturing efficiency while providing a product that meets increasing consumer expectations.

Accordingly, it would be advantageous to have improved materials for making candles and other wax products, would be environmentally and economically desirable if such materials were biodegradable and derived from renewable raw materials, such as natural oils.

SUMMARY

The present disclosure provides a flexible wax composition having about 20 wt % to about 45 wt % monoacylglycerides, about 28 wt % to about 40 wt % diacylglycerides, and about 10 wt % to about 45 wt % acylglyceride polymers, wherein acylglyceride polymers are compounds that contain one or more dimerized fatty acid residue and a plurality of glycerol moieties.

The present disclosure also provides a flexible wax composition wherein about 40 wt % to about 75 of the composition is acylglycerides having a weight average molecular weight (Mw) of about 200 Da to about 580 Da, and at least 10 wt % of the composition is acylglycerides having a weight average molecular weight of about 900 Da to about 3000 Da.

The present disclosure further provides a method of making a flexible wax composition. The method comprises mixing fatty acid and/or oil, a fatty acid dimer, and glycerin to form a reaction mixture; and adding a caustic or enzymatic catalyst to the mixture to facilitate a transesterification reaction until the mixture achieves an acid value (AV) of less than 1.5, so as to obtain a flexible wax composition.

The flexible wax compositions described herein are useful for candles, coatings, broadsizing for oriented strand board (OSB), tire and rubber applications, polyvinyl chloride (PVC) piping, crayons, and personal care products. In many of these applications, waxes are desired which have certain physical characteristics, e.g., in terms of drop point, hardness or malleability, that permit the material to be readily formed into the desired product. In the case of candles specifically, it is desirable for the wax to have properties which can improve ease of manufacturing while providing a wax producing have a pleasing appearance and feel.

Advantages, some of which are unexpected, are achieved by embodiments of the present disclosure. For example, various compositions described herein advantageously resist cracking when deformed or subjected to cold temperatures. The flexible wax compositions have an average creep stiffness (at 60 seconds and measured at 22° C.) of less than about 30 MPa, less than about 25 MPa, less than about 20 MPa, less than about 15 MPa, or less than about 10 MPa. Reduced average creep stiffness reflects improved resistance to cracking. Various compositions herein demonstrate lower average creep stiffness and thus increased flexibility and cracking resistance compared to conventional wax formulations.

The flexible wax composition of the present disclosure also has improved manufacturing properties. For example, in various embodiments, the flexible wax composition cools faster than conventional paraffin waxes and, during cooling, the composition does not show any detrimental increase in interior temperature such as that displayed in some conventional waxes. Consistent cooling is important during candle formation and it is advantageous to avoid compositions that exhibit heats of crystallization that increase internal temperature during cooling. There is also another challenge in candle manufacturing that relates to the amount of adhesion to the glass containers in which candles are formed. A candle having complete adhesion to the glass will have better consumer appeal than a candle which partially adheres to the glass. Moreover, a candle which lacks sufficient adhesion may rattle in the container. Various flexible wax compositions of the present disclosure have the advantage of offering substantially improved adhesion to glass containers. Such improved adhesion properties are also expected to improve use of the wax for various coating-based applications.

As a further advantage, various compositions described herein are natural oil-based waxes and thus have the advantage of comprising biodegradable, renewable, and environmentally-friendly components. For example, the flexible wax composition of the present disclosure can be prepared from natural oils and yet can offer the above-described advantages of resistance to cracking, faster cooling and improved glass adhesion.

DETAILED DESCRIPTION

Figure 1:
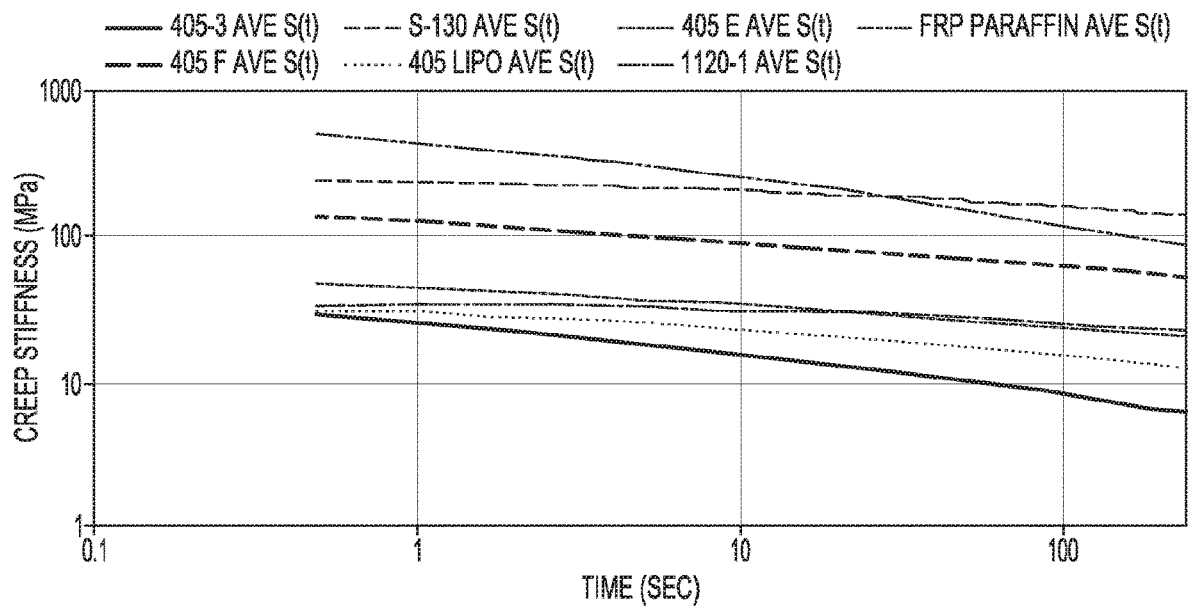
FIG. 1 shows a plot depicting the average creep stiffness (MPa) over time (seconds) for various wax compositions. The plot shows data for a fully refined paraffin wax, various exemplified flexible wax compositions that are described herein, and a comparative wax formulation prepared without the fatty acid dimer.

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

As used herein, the singular forms "a," "an," and "the" include plural referents unless the context clearly dictates otherwise. For example, reference to "a substituent" encompasses a single substituent as well as two or more substituents, and the like. It is understood that any term in the singular may include its plural counterpart and vice versa.

The term "or" is used to refer to a nonexclusive "or" unless otherwise indicated. The statement "at least one of A and B" has the same meaning as "A, B, or A and B."

In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Any, publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

As used herein, the terms "for example," "for instance," "such as," or "including" are meant to introduce examples that further clarify more general subject matter. Unless otherwise specified, these examples are provided only as an aid for understanding the applications illustrated in the present disclosure, and are not meant to be limiting in any fashion.

In the methods described herein, the acts can be carried out in any order without departing from the principles of the disclosure, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

As used herein, the following terms have the following meanings unless expressly stated to the contrary.

As used herein, the term "natural oil" may refer to oil derived from plants or animal sources. The term "natural oil" includes natural oil derivatives, unless otherwise indicated. Examples of natural oils include, but are not limited to, vegetable oils, algae oils, animal fats, tall oils, derivatives of these oils, combinations of any of these oils, and the like. Representative non-limiting examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, camelina oil, pennycress oil, hemp oil, algal oil, and castor oil. Representative non-limiting examples of animal fats include lard, tallow, poultry fat, yellow grease, and fish oil. Tall oils are by-products of wood pulp manufacture. In some aspects, the natural oil may be refined, bleached, and/or deodorized. In some aspects, the natural oil may be partially or fully hydrogenated. In some aspects, the natural oil is present individually or as mixtures thereof.

As used herein, the term "natural oil derivatives" may refer to the compounds or mixture of compounds derived from the natural oil using any one or combination of methods known in the art. Such methods include saponification, transesterification, esterification, interesterification, hydrogenation (partial or isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil.

As used herein, a "natural oil-based" composition means that the composition contains oils and fatty acids which are predominantly, substantially or entirely, derived from natural oils and natural oil derivatives. Examples of natural oil-based waxes include vegetable oil-based waxes and animal oil-based waxes. An example vegetable oil-based wax is a soybean oil-based wax. The natural oil-based wax may, in various embodiments, contain oils which are at least 50%, 55%, 60%, 65%, 70%, 75%, 80%, 85%, 90%, 95%, 99%, 99.9%, 99.99% or about 100% natural oil. In various embodiments, a natural oil-based wax may be substantially free of paraffin. In various further embodiments, the natural oil-based wax may be a non-beeswax natural oil-based wax.

A "monoacylglyceride" refers to a molecule having a glycerol moiety with a single fatty acid residue that is linked via an ester bond. The terms "monoacylglycerol," "monoacylglyceride," "monoglyceride," and "MAG" are used interchangeably herein. Monoacylglycerides include 2-acylglycerides and 1-acylglycerides.

A "diacylglyceride" refers to a molecule having a glycerol moiety having two fatty acid residues linked via ester bonds. The terms "diacylglycerol," "diacylglyceride," "diglyceride," and "DAG" are used interchangeably herein. Diacylglycerides include 1,2-diacylglycerides and 1,3-diacylglycerides.

A "triacylglyceride" refers to a molecule having a glycerol moiety that is linked to three fatty acid residues via ester bonds. The terms "triacylglycerol," "triacylglyceride," "triglyceride," and "TAG" are used interchangeably herein.

An "acylglyceride" refers to a molecule having at least one glycerol moiety with at least one fatty acid residue that is linked via an ester bond. For example, acylglycerides can include monoacylglycerides, diacylglycerides, triacylglycerides and acylglyceride polymers. The group acylglycerides can be further refined by additional descriptive terms and can be modified to expressly exclude or include certain subsets of acylglycerides. For example, the phrase mono- and di-acylglycerides refers to MAGs and DAGs, while the phrase non-MAG/non-DAG acylglycerides refers to a group of acylglycerides which exclude MAGs and DAGs. As another example, acylglycerides comprising a C36 dimeric fatty acid residue refers only to those acylglycerides having the specified residue.

An "acylglyceride polymer" refers to a compound having two or more glycerol moieties linked together by at least one diacid linking residue, such as a dimerized fatty acid residue. For example, the acylglyceride polymer can refer to a compound having the structure of Formula I:

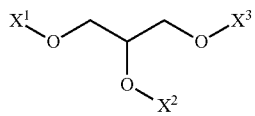

Formula I

Each occurrence of $X^1$, $X^2$ and $X^3$ is independently H, a fatty acid residue, a dimerized fatty acid residue, or a residue having a structure of Formula II:

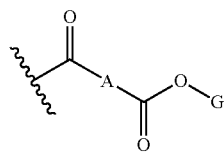

Formula II

In Formula I, at least one of $X^1$, $X^2$ and $X^3$ is a residue having a structure according to Formula II.

G is a substituted or unsubstituted glycerol unit. G can be a monoacylglyceride, diacylglyceride or triacylglyceride. For example, G can be the structure of Formula I wherein one of $X^1$, $X^2$ and $X^3$ is replaced with a bond. Thus, in a further example of Formula I, each occurrence of $X^1$, $X^2$ and $X^3$ is independently H, a non-dimerized fatty acid residue, a dimerized fatty acid residue, or a residue having a structure according to Formula IIa or Formula IIb, and at least one of $X^1$, $X^2$ and $X^3$ is a residue having a structure according to Formula IIa or Formula IIb:

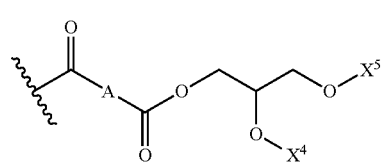

Formula IIa

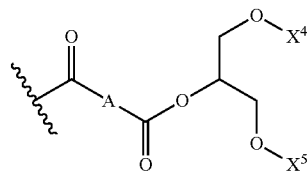

Formula IIb

A is any suitable divalent group. For example, A can be —$R^1$—Z—$R^2$— or —$R^1$-$R^2$—. Thus, in another example of Formula I, each occurrence of $X^1$, $X^2$ and $X^3$ is independently H, a non-dimerized fatty acid residue, a dimerized fatty acid residue, or a residue having a structure according to Formula IIc, Formula IId, Formula IIe or Formula IIf, and at least one of $X^1$, $X^2$ and $X^3$ is a residue having a structure according to Formula IIc, Formula IId, Formula IIe or Formula IIf:

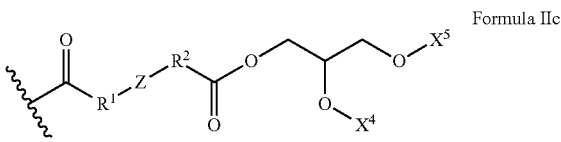

Formula IIc

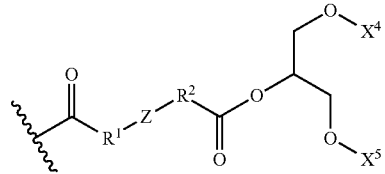

Formula IId

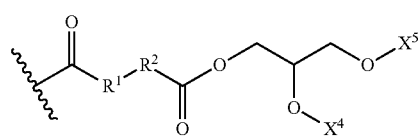

Formula IIe

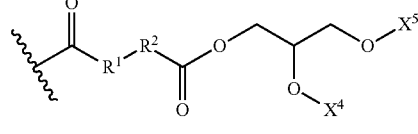

Formula IIf

Each occurrence of $X^4$ and $X^5$ is independently H, a non-dimerized fatty acid residue, a dimerized fatty acid residue; or a residue having a structure according to Formula IIc, Formula IId, Formula IIe or Formula IIf.

$R^1$ and $R^2$ are each independently a substituted or unsubstituted aliphatic group. The aliphatic group can correspond to a saturated fatty acid side chain or an unsaturated fatty acid side chain having one, two, three or more double bonds. The aliphatic group can be, for example, 1 to 30 carbons, 5 to 25 carbons, 7 to 21 carbons, 12 to 2.1 carbons, 15 to 19 carbons, or 17 carbons. Optionally, $R^1$ and $R^2$ can be substituted and example substituents include alkyl, alcohol, halide, and oxygen so as to form an epoxide ring. $R^1$ and $R^2$ can be a saturated or unsaturated linear aliphatic group having 7, 9, 11, 13, 15, 17, 19 or 21 carbons. When $R^1$ and $R^2$ are each a 17-carbon saturated or unsaturated group, the resulting dimerized fatty acid residue has 36 carbons. $R^1$ and $R^2$ can comprise hydrogen, carbon, oxygen, and nitrogen atoms; or $R^1$ and $R^2$ can consist of carbon, hydrogen, and oxygen atoms; or $R^1$ and $R^2$ can consist of carbon and hydrogen atoms. The linking group Z is a bond, an oxygen atom, or any other suitable linking group. The linking group Z may be attached to $R^1$ and $R^2$ via any position.

As another example, the acyl glyceride polymer can refer to a compound having the structure of Formula III:

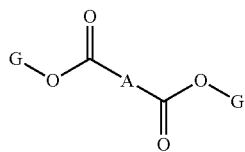

Formula III

G is a substituted or unsubstituted glycerol unit. G can be a monoacylglyceride, diacylglyceride or triacylglyceride. For example, G can be the structure of Formula I wherein one of $X^1$, $X^2$ and $X^3$ is replaced with a bond.

A is a divalent group. For example, A can be —$R^1$—Z—$R^2$— or —$R^1$-$R^2$— in which each of $R^1$ and $R^2$ is independently a divalent aliphatic group that corresponds to a fatty acid side chain, e.g., a 11 to 21 carbon alkyl or alkenyl chain, and the linking group Z is a bond or an oxygen bound to any position of $R^1$ and $R^2$.

As another example, the acylglyceride polymer can refer to a compound having the structure of Formula IVa, Formula IVb, and/or Formula IVc:

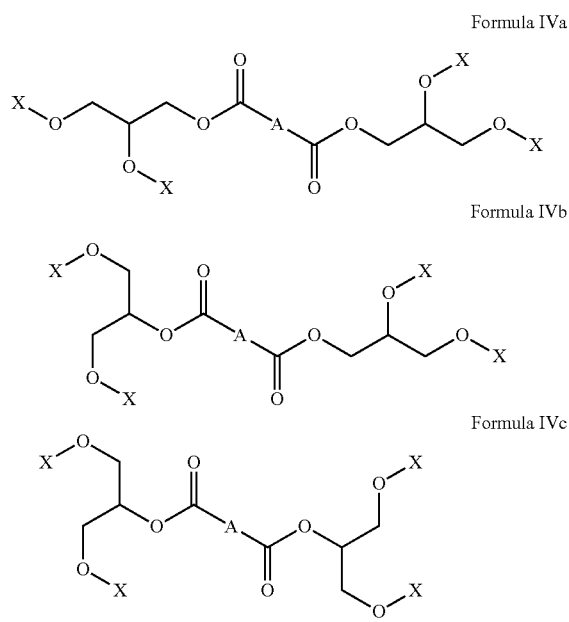

Formula IVa

Formula IVb

Formula IVc

Each occurrence of X is H, a non-dimerized fatty acid residue, a dimerized fatty acid residue, or a residue having a structure of Formula II, Formula IIa, Formula IIb, Formula IIc, Formula IId, Formula IIe, Formula IIf or Formula IIg.

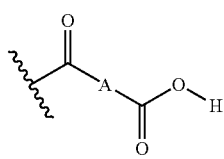

Formula IIg

A is a divalent group. For example, A can be —$R^1$—Z—$R^2$— or —$R^1$-$R^2$— in which each of $R^1$ and $R^2$ is independently a divalent aliphatic group that corresponds to a fatty acid side chain, e.g., a 11 to 21 carbon alkyl or alkenyl chain, and the linking group Z is a bond or an oxygen bound to any position of R' and $R^2$.

As another example, the acylglyceride polymer can refer to a polymer comprising monomer residues according to the following structures:

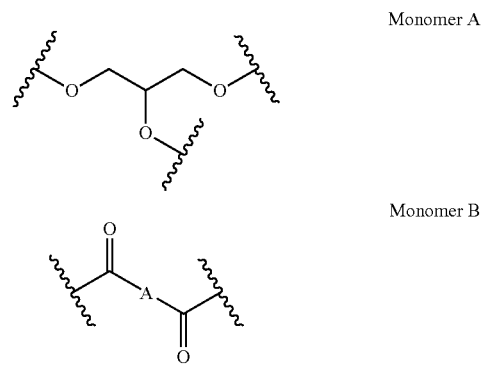

Monomer A

Monomer B

Each instance of Monomer A is directly linked to 1, 2 or 3 of Monomer B. Each position of Monomer A that is not linked to Monomer B is terminated. Monomer A is terminated by H or a fatty acid residue.

Each instance of Monomer B is linked to 1 or 2 of Monomer A. Each position of Monomer B that is not linked to Monomer A is terminated. Monomer B is terminated by —OH. In a further example, substantially all instances of Monomer B are linked to 2 of Monomer A, Monomer B is a diacid linking residue and A is a divalent linking group. For example, Monomer B can be a dimerized fatty acid residue. In a further embodiment, A can be can be —$R^1$—Z—$R^2$— or —$R^1$-$R^2$—, in which each of $R^1$ and $R^2$ is independently a divalent aliphatic group that corresponds to a fatty acid side chain, e.g., a 11-21-carbon alkyl or alkenyl chain, and the linking group Z is a bond or an oxygen bound to any position of $R^1$ and $R^2$.

Acylglyceride polymers thus include compounds having a plurality of glycerol moieties and plurality of diacid linking residues. An acylglyceride polymer can be a linear polymer or a crosslinked polymer. Unless otherwise provided, the term acylglyceride polymer also includes compounds having only two glycerol moieties linked together by a single diacid linking residue. At the same time, the term acylglyceride polymer can refer to larger compounds, such as compounds having 2 or more, 10 or more, 20 or more, 30 or more, 40 or more, 50 or more, 75 or more, 100 or more, 250 or more, 500 or more, or 1,000 or more glycerol units, or compounds having 2 or more, 10 or more, 20 or more, 30 or more, 40 or more, 50 or more, 75 or more, 100 or more, 250 or more, 500 or more, or 1,000 or more dimerized fatty acid linking residues, or any combination of such features.

The term "diacid linking residue" refers to a residue having the structure:

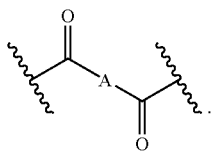

A diacid linking residue is a divalent group which can function to link two separate portions of a molecule. A diacid linking residue contains two terminal acyl groups which are separated by a divalent group A. The divalent group A can be any suitable divalent linking group. For example, A can be a hydrocarbon, such as a divalent alkyl group, a divalent alkenyl group, a divalent aromatic group, or a combination thereof. As another example, A can be —$R^1$—Z—$R^2$— or —$R^1$-$R^2$—, in which each of $R^1$ and $R^2$ is independently a divalent aliphatic group that corresponds to a fatty acid side chain, e.g., a 11 to 21 carbon alkyl or alkenyl chain, and the linking group Z is a bond or an oxygen bound to any position of $R^1$ and $R^2$. As a further example, the diacid linking residue is a dimerized fatty acid residue.

The term "weight average molecular weight" as used herein refers to $M_w$, which is equal to $\Sigma M_i^2 n_i / \Sigma M_i n_i$, where $n_i$ is the number of molecules of molecular weight $M_i$. In various examples, the weight-average molecular weight can be determined using light scattering, small angle neutron scattering, X-ray scattering, and sedimentation velocity.

The term "fatty acid" as used herein can refer to a molecule comprising a hydrocarbon chain and a terminal carboxylic acid group. As used herein, the carboxylic acid group of the fatty acid may be modified or esterified, for example as occurs when the fatty acid is incorporated into a glyceride or another molecule (e.g., COOR, where R refers to, for example, a carbon atom). Alternatively, the carboxylic acid group may be in the free fatty acid or salt form (i.e., COO" or COOH). The 'tail' or hydrocarbon chain of a fatty acid may also be referred to as a fatty acid chain, fatty acid sidechain, or fatty chain. The hydrocarbon chain of a fatty acid will typically be a saturated or unsaturated aliphatic group. A fatty acid having N number of carbons, will typically have a fatty acid side chain having N−1 carbons. However, the subject application also relates to modified forms of fatty acids, e.g., dimerized fatty acids, and thus the term fatty acid may be used in a context in which the fatty acid has been substituted or otherwise modified as described. For example, in various embodiments, a fatty acid may be dimerized with another fatty acid to result in a dimerized fatty acid. Unless otherwise specified, the term fatty acid as used herein refers to a non-dimerized fatty acid, while the term dimerized fatty acid and the like refer to the dimer forms of fatty acids.

A "fatty acid residue" is a fatty acid in its acyl or esterified form.

The levels of particular types of fatty acids may be provided herein in percentages out of the total fatty acid content of an oil or wax. Unless specifically noted otherwise, such percentages are weight percentages based on the total fatty acids, including free fatty acids and esterified fatty acids as calculated experimentally.

A "saturated" fatty acid is a fatty acid that does not contain any carbon-carbon double bonds in the hydrocarbon chain. An "unsaturated" fatty acid contains one or more carbon-carbon double bonds. A "polyunsaturated" fatty acid contains more than one such carbon-carbon double bond while a "monounsaturated" fatty acid contains only one carbon-carbon double bond. Carbon-carbon double bonds may be in one of two stereoconfigurations denoted cis and trans. Naturally-occurring unsaturated fatty acids are generally in the "cis" form.

Non-limiting examples of fatty acids include C8, C10, C12, C14, C16 (e.g., C16:0, C16:1), C18 (e.g., C18:0, C18:1, C18:2, C18:3, C18:4), C20 and C22 fatty acids. For example, the fatty acids can be caprylic (8:0), capric (10:0), lauric (12:0), myristic (14:0), palmitic (16:0), stearic (18:0), oleic (18:1), linoleic (18:2) and linolenic (18:3) acids.

The fatty acid composition of an oil can be determined by methods well known in the art. The American Oil Chemist's Society (AOCS) maintains analytical methods for a wide variety of tests performed on vegetable oils. Hydrolysis of the oil's components to produce free fatty acids, conversion of the free fatty acids to methyl esters, and analysis by gas-liquid chromatography (GLC) is the universally accepted standard method to determine the fatty acid composition of an oil sample. The AOCS Procedure Ce 1-62 describes the procedure used.

The terms "fatty acid dimer" and "dimerized fatty acid" are interchangeably used herein and refer generally to a compound containing two fatty acid subunits in which the respective fatty acid side chains are covalently bound to each other, e.g., via a bond or a linking group. Thus, as described herein, the fatty acid dimer is a covalent fatty dimer. The fatty acid dimer can be a heterodimer or a homodimer. As used herein, the carboxylic acid group of the fatty acid dimer may be modified or esterified, for example as occurs when the fatty acid dimer is incorporated into a glyceride or is attached to another molecule. Suitable fatty acid dimers are commercially available, for example, Radiacid 0960 Hydrogenated Standard Dimer and Radiacid 0970 Distilled Dimer Acid (Oleon N.V., Belgium) and UNIDYME 18 Dimer Acid (Kraton Corporation, Houston, Tex.).

The term "fatty acid dimer residue" or "dimerized fatty acid residue" as used herein, refers generally to a fatty acid dimer that is linked by at least one ester bond to a parent compound, such as a glycerol or acylglyceride. A fatty acid dimer residue corresponds to a fatty acid dimer where one or more terminal carboxylic acid has been replaced with an acyl group. A fatty acid dimer residue is a type of linking group or linking residue, which can link two separate portions of a molecule via ester bonds. Suitable fatty acid dimer residues include those derived from commercially available fatty acid dinners.

As an example, the dimerized fatty acid residue can have the structure:

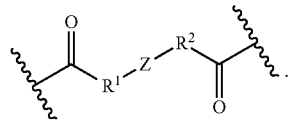

In the example dimerized fatty acid residue, $R^1$ and $R^2$ are each independently a substituted or unsubstituted aliphatic group. The aliphatic group can correspond to a saturated fatty acid side chain or an unsaturated fatty acid side chain having one, two, three or more double bonds. The aliphatic group can be, for example, 1 to 30 carbons, 5 to 25 carbons, 7 to 21 carbons, 12 to 21 carbons, 15 to 19 carbons, or 17 carbons. Optionally, $R^1$ and $R^2$ can be substituted and example substituents include alkyl, alcohol, halide, and oxygen so as to form an epoxide ring. $R^1$ and $R^2$ can be a saturated or unsaturated linear aliphatic group having 7, 9, 11, 13, 15, 17, 19 or 21 carbons. When $R^1$ and $R^2$ are each a 17-carbon saturated or unsaturated group, the resulting dimerized fatty acid residue has 36 carbons. $R^1$ and $R^2$ can comprise hydrogen, carbon, oxygen, and nitrogen atoms; or $R^1$ and $R^2$ can consist of carbon, hydrogen, and oxygen atoms; or $R^1$ and $R^2$ can consist of carbon and hydrogen atoms.

The linking group Z is a bond, an oxygen atom, or any other suitable linking group. The linking group Z may be attached to $R^1$ and $R^2$ via any position. For example, the linking group Z may be attached to a position at $R^1$ and $R^2$ other than the terminal carbons. As another example, $R^1$ and $R^2$ can be a linear aliphatic group which corresponds to a fatty acid side chain, and the linking group Z can be attached at omega number 2, 3, 4, 5, 6, 7, 8, 9, 10, 11, 12, 13, 14, 15, 16, 17, etc., or, alternatively the linking group Z can be linked at the terminal ($\omega$-1) carbon. In another example, the Z group represents multiple bonds such that $R^1$ and $R^2$ are linked so as to form a carbocyclic or heterocyclic ring between them. When Z is a bond, the dimerized fatty acid residue may have the structure:

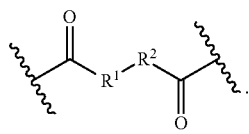

A "plurality" refers to two or more. For example, a polymeric compound having a plurality of glycerol units can have 2 or more glycerol units, 1.0 or more glycerol units, 100 or more glycerol units, 1,000 or more glycerol units, etc.

A "drop point" or "dropping point" generally refers to the temperature at which a wax softens and becomes sufficiently fluid to flow as determined under the conditions of a given standardized test. As used herein, drop points are determined via AOCS Standard Procedure Cc 18-80, (Official Methods and Recommended Practices of the American Oil Chemists' Society, 7th Edition). Drop point is similar to melting point in that it reflects the thermal characteristics of a compound, however, drop point can be useful for materials which do not have a defined melting point.

The "average creep stiffness" of a wax composition can be determined by Standard Test Method for Determining The Flexural Creep Stiffness of Asphalt Binder Using the Bending Beam Rheometer test, ASTM Method D 6648-08, run at or about room temperature (e.g., about 22° C. to about 25° C.) using a creep load of about 500 N, which is a lower creep load than the normal 950N used in this method. As used herein, the test was performed in triplicate at 22° C. under a constant load of 490±50 N to report an average of the three tests. The creep behavior can be fundamentally related to relaxation properties through theories of viscoelasticity. For simplicity the creep and relaxation properties of the waxes as demonstrated by the Bending Beam Rheometer test are herein referred to as "flexibility".

The "acid value" (AV) is defined as the weight of KOH in mg needed to neutralize the organic acids present in Ig of test sample and it is a measure of the free fatty acids present in the composition, AV can be determined by the AOCS Official Method Cd 3d-63.

Flexible Wax Composition

The flexible wax composition described herein has a unique composition which provides a wax that is more flexible than traditional vegetable wax and paraffin wax. This flexible wax composition is achieved through the use of dimer fatty acids and either fatty acids or triglycerides that are chemically or enzymatically esterified with glycerin. The dimer fatty acid acts as a crosslinker between glycerides. Typically, in wax manufacturing, one skilled in the art is intending to reduce the average molecular weight of acylglycerides by removing larger components such as DAGs and TAGs. Here, surprisingly, use of larger molecular weight components has provided a flexible wax composition which is advantageously resistant to cracking and has improved manufacturing properties, such as faster cooling and improved glass adhesion.

The present disclosure provides a flexible wax composition comprising monoacylglycerides, diacylglycerides and acylglyceride polymers. About 20 wt % to about 45 wt % of the composition is monoacylglycerides, about 28 wt % to about 40 wt % of the composition is diacylglycerides and at least 10 wt % of the composition is acylglyceride polymers. The acylglyceride polymers contain one or more dimerized fatty acid residue and a plurality of glycerol moieties.

In various embodiments, the acylglyceride polymers have a structure according to any of the acylglyceride polymer structures described herein. For example, the acylglyceride polymers can have a structure according to one or more of Formula I, Formula II, Formula IIa, Formula IIb, Formula IIc, Formula IId, Formula IIe, Formula IIf, Formula IIg, Formula III, Formula IVa, Formula IVb, or Formula IVc, or any combination or permutation thereof. As a further example, the acylglyceride polymers can have monomers according to Monomer A and Monomer B.

In various embodiments, acylglyceride polymers can be about 10 wt % to about 45 wt % of the composition. For example, about 10 wt % to about 38 wt %, about 10 wt % to about 35 wt %, about 10 wt % to about 30 wt %, about 10 wt % to about 25 wt %, about 10 wt % to about 20 wt %, about 14 wt % to about 38 wt %, about 14 wt % to about 35 wt %, about 14 wt % to about 30 wt %, about 14 wt % to about 25 wt %, or about 14 wt % to about 20 wt % of the composition is acylglyceride polymer.

The composition may have at least 10 wt %, 11 wt %, 12 wt %, 13 wt %, 14 wt %, 15 wt %, 20 wt %, 25 wt %, 30 wt %, 35 wt % or 40 wt % acylglyceride polymers; the composition may have up to 15 wt %, 20 wt %, 25 wt %, 30 wt %, 35 wt %, 40 wt % or 45 wt % acylglyceride polymers; or both.

Monoacylglycerides can be present, for example, at about 21 wt % to about 45 wt %, about 25 wt % to 40 wt %, or 21 wt % to about 40 wt % of the composition. Diacylglycerides can be present, for example, at about 20 wt % to about 40 wt %, about 25 wt % to 40 wt %, or 30 wt % to about 39 wt % of the composition. Triacylglycerides can be present, for example, at about 1 wt % to about 17 wt %, at about 1 wt % to about 10 wt %, at about 3 wt % to about 8 wt %, or about 1 wt % to 5 wt % of the composition. In various embodiments, about 40 wt % to about 75 wt % of the composition is monoacylglycerides and diacylglycerides.

The composition can comprise minimal amounts of free fatty acids and glycerin. For example, composition can comprise less than about 2 wt % free fatty acids and free glycerin. In another embodiment, the composition can comprise less than about 1 wt %, about 2.5 wt %, less than about 5 wt %, or less than about 10 wt %, free fatty acids, free glycerin and triacylglycerides.

In an example embodiment, about 21 wt % to about 40 wt % of the composition is monoacylglycerides, about 30 wt % to about 39 wt % of the composition is diacylglycerides and about 14 wt % to about 38 wt % of the composition is acylglyceride polymers. In a further embodiment, the composition contains about 2 wt % to about 17 wt % triacylglycerides.

The flexible wax composition of the present invention can further be described in terms of average molecular weight distribution, which may be determined by gel permeation chromatography (GPC).

For example, in various embodiments, at least 10 wt % of the composition is acylglycerides that have a weight average molecular weight of 900 Da, 1000 Da, 1100 Da, 1200 Da, 1300 Da, 1400 Da, 1500 Da, 1600 Da, 1700 Da, 1800 Da, 1900 Da, 2000 Da or more. In various embodiments, about 10 wt % to about 45 wt % of the composition is acylglycerides that have a weight average molecular weight of 900 Da, 1000 Da, 1100 Da, 1200 Da, 1300 Da, 1400 Da, 1500 Da, 1600 Da, 1700 Da, 1800 Da, 1900 Da, 2000 Da or more.

In another embodiment, the composition may have at least 11 wt %, 12 wt %, 13 wt'%©, 14 wt %, 15 wt %, 20 wt %, 25 wt %, 30 wt %, 35 wt % or 40 wt % acylglycerides that have a weight average molecular weight of 900 Da to 3000. In further embodiments, the composition may have up to 15 wt %, 20 wt %, 25 wt %, 30 wt %, 35 wt %, 40 wt % or 45 wt % is acylglycerides that have a weight average molecular weight of 900 Da to 3000. In various embodiments, about 10 wt % to about 45 wt % of the composition is acylglycerides that have a weight average molecular weight of 900 Da to 3000 Da, 1000 Da to 3000 Da, 1200 Da to 3000 Da or 1500 Da to 3000 Da.

In further embodiments, about 10 wt % to about 38 wt %, about 10 wt % to about 35 wt %, about 10 wt % to about 30 wt %, about 10 wt % to about 25 wt %, about 10 wt % to about 20 wt %, about 14 wt % to about 38 wt %, about 14 wt % to about 35 wt %, about 14 wt % to about 30 wt %, about 14 wt % to about 25 wt %, or about 14 wt % to about 20 wt % of the composition is acylglycerides that have a weight average molecular weight of 900 Da to 3000 Da.

In various further embodiments, about 20 wt % to about 60 wt % of the composition is acylglyceride having a weight average molecular weight of 580 Da to 3000 Da. In further embodiments, about 20 wt % to about 50 wt %, about 20 wt % to about 40 wt %, about 20 wt % to about 35 wt %, about 20 wt % to about 30 wt %, about 25 wt % to about 50 wt %, about 25 wt % to about 40 wt %, about 25 wt % to about 35 wt %, or about 25 wt % to about 30 wt % of the composition is acylglyceride having a weight average molecular weight of 580 Da to 3000 Da. For example, about 25 wt %, 26 wt %, 27 wt %, 28 wt %, 29 wt %, or 30 wt % of the composition can be acylglyceride having a weight average molecular weight of 580 to 900 Da.

The composition may have at least 15 wt %, 20 wt %, 25 wt % or 30 wt % is acylglyceride having a weight average molecular weight of 580 or greater; or at least 15 wt %, 20 wt %, 25 wt % or 30 wt % is acylglyceride having a weight average molecular weight of 580 Da to 3000 Da. In various embodiments, the composition has less than 60 wt %, 55 wt % or 50 wt % is acylglyceride having a weight average molecular weight of 580 or greater; or less than 60 wt %, 55 wt % or 50 wt % is acylglyceride having a weight average molecular weight of 580 Da to 3000 Da. For example, about 13 wt %, 14 wt % or 15 wt %, of the composition can be acylglyceride with a weight average molecular weight of 580 to 3000 Da.

In various embodiments, the composition has less than 25 wt %, 24 wt %, 23 wt %, 22 wt %, 21 wt %, 20 wt %, 19 wt %, 18 wt %, 17 wt %, 16 wt %, 15 wt % or 14 wt % is acylglyceride having a weight average molecular weight of 580 to 900 Da. For example, about 13 wt %, 14 wt % or 15 wt % of the composition can be acylglyceride having a weight average molecular weight of 580 to 900 Da.

The flexible wax composition described herein has an average creep stiffness (at 60 seconds and measured at 22° C.) of less than about 30 MPa, less than about 25 MPa, less than about 20 MPa, less than about 15 MPa, and less than about 10 MPa.

The flexible wax composition has a drop point ranging from about 50-60° C. The flexible wax composition is derived from a natural oil or natural oil derivative. The flexible wax composition can be used in candles, paper coatings, box coatings, fruit coatings, broadsizing for OSB, tire and rubber, polyvinyl chloride (PVC) piping, crayons, and personal care.

The present disclosure also describes a flexible wax composition as characterized by a combination of polymers, MAGs, DAGs, and TAGs. In one embodiment, the flexible wax composition comprises about 10-45 wt % polymer, about 20-45 wt % MAGs, about 28-40 wt % DAGs, and about 10-17 wt % TAGs. In another embodiment, the flexible wax composition comprises about 14-38 wt % polymer, about 21-40 wt % MAGs, about 30-39 wt % DAGs, and about 13-17 wt % TAGs.

The present disclosure also provides a flexible wax composition, which comprises monoacylglycerides, diacylglycerides and high-molecular weight acylglycerides having a weight average molecular weight of about 900 Da to about 3000 Da. About 40 wt % to about 75 wt % of the composition is monoacylglycerides and diacylglycerides having a weight average molecular of about 200 Da to about 580 Da; and at least 10 wt % of the composition is acylglycerides having a weight average molecular weight of about 900 Da to about 3000 Da.

Dimerized Fatty Acid Residue

The flexible wax composition of the present disclosure may contain acylglycerides having a dimerized fatty acid residue, for example, at least 10 wt %, 15 wt %, 20 wt %, 25 wt %, 30 wt %, 35 wt %, or 40 wt % of the flexible wax composition. The acylglycerides containing one or more dimerized fatty acid residue may contain one, two, or more glycerol units. One example of such acylglycerides are the acylglyceride polymers described herein. Another example is acylglycerides having a single glycerol and one or more dimerized fatty acid residue.

The dimerized fatty acid residue may have from 20 to 60 carbons. In various embodiments, the dimerized fatty acid residue has 30 to 40 carbons. The dimerized fatty acid residue can be a 36-carbon residue. For example, the dimerized fatty acid residue can be a linoleic acid dimer residue, an oleic acid dimer residue, or an oleic acid-linoleic acid heterodimer residue.

The dimerized fatty acid residue can be an esterified form of commercially available fatty acid dimers, for example, Radiacid 0960 Hydrogenated Standard Dimer and Radiacid 0970 Distilled Dimer Acid (Oleon N.V., Belgium) and UNIDYME 18 Dimer Acid (Craton Corporation, Houston, Tex.).

As an example, the dimerized fatty acid residue can have structure:

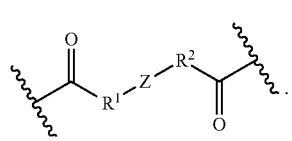

$R^1$ and $R^2$ are each independently defined divalent fatty acid chains so that $R^1$ and $R^2$ may be the same or different. When $R^1$ and $R^2$ are the same, the dimerized fatty acid residue represents a fatty acid homodimer. When $R^1$ and $R^2$ are the different, the dimerized fatty acid residue represents a fatty acid heterodimer. In various embodiments, each of $R^1$ and $R^2$ is independently a substituted or unsubstituted $C_7$-$C_{21}$ aliphatic group corresponding to a saturated fatty acid side chain or an unsaturated fatty acid side chain having one, two, three or more double bonds. $R^1$ and $R^2$ can represent substituted forms of the side chains of naturally occurring fatty acids. For example, $R^1$ and $R^2$ may each independently be a saturated or unsaturated linear aliphatic group having 7, 9, 11, 13, 15, 17, 19 or 21 carbons. When $R^1$ and $R^2$ are each a 17-carbon saturated or unsaturated group, the resulting dimerized fatty acid residue has 36 carbons. $R^1$ and $R^2$ can comprise hydrogen, carbon, oxygen, and nitrogen atoms; or $R^1$ and $R^2$ can consist of carbon, hydrogen, and oxygen atoms; or $R^1$ and $R^2$ can consist of carbon and hydrogen atoms.

The linking group Z is a bond, an oxygen atom, or any other suitable linking group. The linking group Z may be attached to $R^1$ and $R^2$ via any position. When Z is a bond, the dimerized fatty acid residue may have the structure:

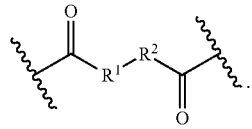

Non-limiting examples of a dimerized fatty acid residue are residues having the structure:

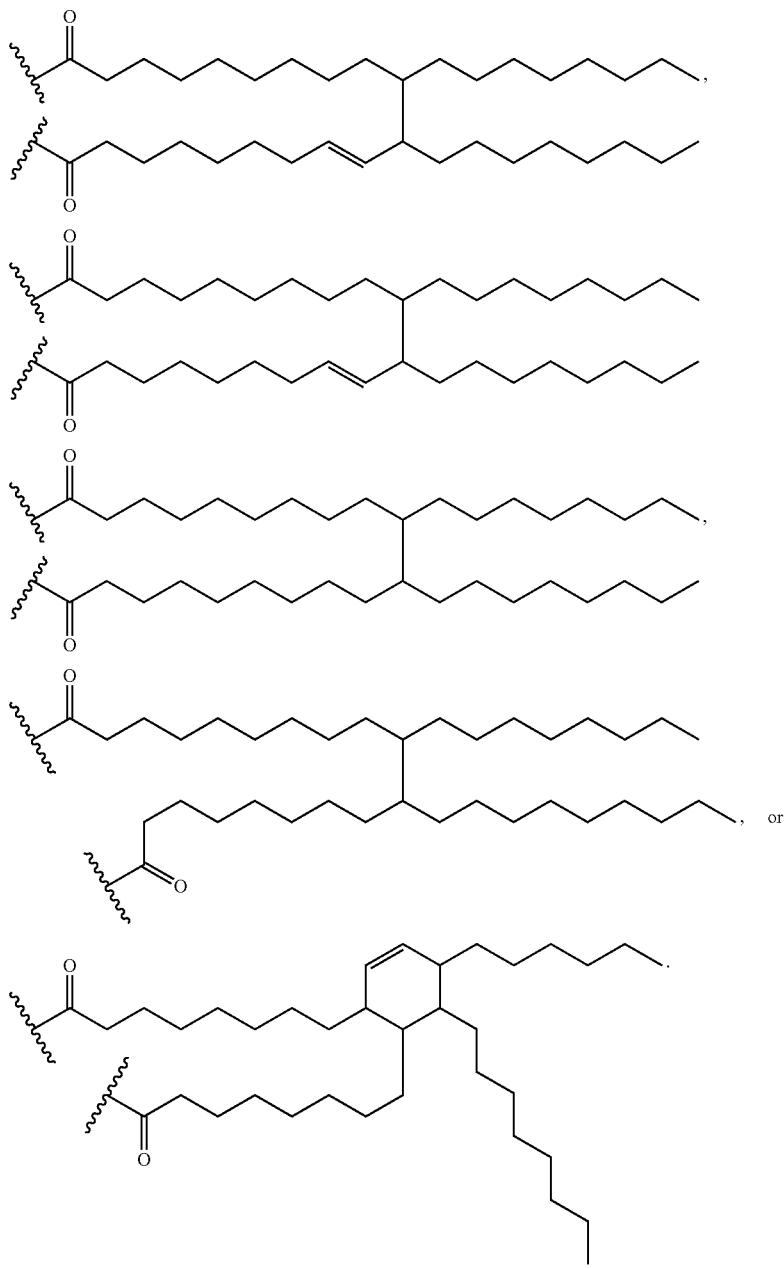

Non-limiting examples of $R^1$ and/or $R^2$ are:

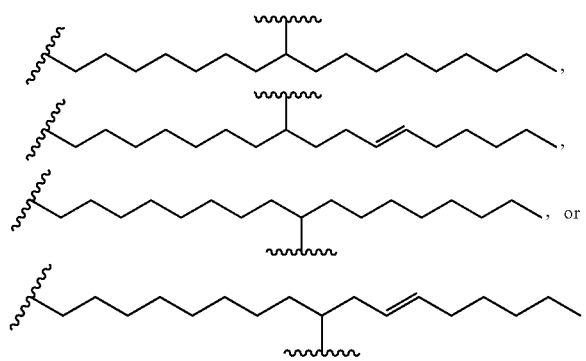

Dimerization of fatty acids can commonly result in formation of a mixture of dimer structures. Thus, the compositions described herein can, in various embodiments, contain a plurality of differing structures corresponding to dimerized fatty acid residues. Unless stated otherwise, a composition that is defined by the presence of one structure of dimerized fatty acid residue does not imply that other, additional dimerized fatty acid residues are absent.

Method of Preparing Flexible Wax Composition

The present disclosure also provides a method of making a flexible wax composition. The method involves mixing one or more fatty acid and/or oil, a fatty acid dimer, and glycerin. The resulting mixture is treated with an esterification catalyst which induces esterification and transesterification. The reaction is allowed to proceed until the reaction mixture reaches an acid value of less than 1.5 so as to provide a flexible wax composition.

The oil can be a natural oil, including a vegetable oil or an animal oil. Examples of oil include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, Jatropha oil, mustard oil, camelina oil, pennycress oil, hemp oil, algal oil, castor oil, lard, tallow, poultry fat, yellow grease, fish oil, or mixtures thereof. Fatty acids can also be directly added to the mixture and may, for example, be derived from any of the aforementioned oils but may be added separately so as to better control the resulting physical properties of the wax.

In various embodiments, the fatty acid dimer has the structure

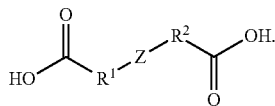

$R^1$ and $R^2$ are each independently defined divalent fatty acid chains so that $R^1$ and $R^2$ may be the same or different. When $R^1$ and $R^2$ are the same, the dimerized fatty acid represents a fatty acid homodimer. When $R^1$ and $R^2$ are the different, the dimerized fatty acid represents a fatty acid heterodimer. In various embodiments, each of $R^1$ and $R^2$ is independently a substituted or unsubstituted $C_7$-$C_{21}$ aliphatic group corresponding to a saturated chain or an unsaturated fatty acid side chain having one, two, three or more double bonds. $R^1$ and $R^2$ can represent substituted forms of the side chains of naturally occurring fatty acids. For example, $R^1$ and $R^2$ may each independent be a saturated or unsaturated linear aliphatic group having 7, 9, 11, 13, 15, 17, 19 or 21 carbons. When $R^1$ and $R^2$ are each a 17-carbon saturated or unsaturated group, the resulting dimerized fatty acid has 36 carbons. $R^1$ and $R^2$ can comprise hydrogen, carbon, oxygen, and nitrogen atoms; or $R^1$ and $R^2$ can consist of carbon, hydrogen, and oxygen atoms; or $R^1$ and $R^2$ can consist of carbon and hydrogen atoms The linking group Z is a bond, an oxygen atom, or a sulfur atom. The linking group Z may be attached to $R^1$ and $R^2$ via any position. When Z is a bond, the dimerized fatty acid may have the structure:

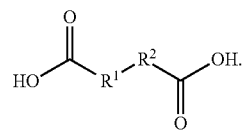

Non-limiting examples of dimerized fatty acids include those commercially available as Radiacid 0960 Hydrogenated Standard Dimer and Radiacid 0970 Distilled Dimer Acid (Oleon N.V., Belgium) and UNIDYME 18 Dimer Acid (Kraton Corporation, Houston, Tex.). The dimerized fatty acid may be derived from a natural oil. As another example, a T18 dimer acid can be used.

The method described herein may comprise the following steps. Fatty acids and/or oils, sourced from natural oils and/or natural derivatives, are pre-melted and heated to a temperature ranging from 60-80° C. before adding to a reaction vessel. The fatty acids can be made up of, but not limited to, C8, C10, C12, C14, C16, C18:0, C18:1, C20, or C22:0 fatty acids, and combinations thereof. The melted fatty acid and/or oils are added to the reaction vessel along with a nitrogen sparge to prevent oxidation. Both dimer acid and glycerin are added to the fatty acids and/or oils to form a reaction mixture.

The reaction mixture typically comprises about 20-30 wt % glycerin and about 15-30 wt % dimer, with the remaining balance being a makeup of fatty acid and/or oil. The reaction mixture is treated to induce chemical or enzymatic transesterification and esterification.

To carry out chemical transesterification, a catalyst can be added at an amount of about 0.1 wt % relative to the reaction mixture. Example catalysts can be potassium hydroxide or calcium hydroxide. The reaction temperature can then be increased to about 200-250° C. This reaction temperature is maintained until an acid value of less than 1.5 is achieved. An acid, for example a mineral acid such as phosphoric acid, can be added at an amount of about 0.2 wt % to neutralize the catalyst with a slight excess. Such acid can be added either before or after the reaction. The reaction mixture can then be cooled to a temperature ranging from about 60-80° C. A filter media, for example acid activated beaching clay, can be added to the reaction mixture in an amount of about 2 wt % relative to the reaction mixture to remove impurities from the wax. The final product, i.e., the flexible wax composition, is then filtered to remove the salt and clay mixture.

To carry out enzymatic transesterification, an enzymatic catalyst can be added at an amount of 2 wt % relative to the reaction mixture. An example enzymatic catalyst can be Lipase Novozyme 435. A vacuum of about 50 torr can be used to remove water as the reaction is taking place. A reaction temperature ranging from about 60-80° C. is maintained until an acid value of less than 1.5 is achieved. The enzymatic catalyst can then be filtered out using an appropriate filter device to obtain the final product, i.e., the flexible wax composition.

Without being bound by any particular theory, it is thought that esterification of the acylglycerides with the fatty acid dimer results in formation of polymers and crosslinked acylglycerides. As a result of the dimer crosslinking, the physical arrangement of the solidified wax product is modified so as to result in a less brittle composition due to a more random alignment of the crystal structure which can thus bend rather than break.

EXAMPLES

TABLE 1

| Materials | Source |
| --- | --- |
| Fatty acid dimer (T18 Dimer) commercially as UNIDYME 18 Dimer Acid | Kraton Corporation, Houston, TX |
| Fatty acids (TRV 1655, TRC 110, TRV 1895) | Twin Rivers Technologies, Quincy, MA |
| Fully hydrogenated soybean oil | Cargill, Incorporated, Wayzata, MN |
| Paraffin wax | Master Rank, Pleasanton, CA |
| S-130 soybean wax | Cargill, Incorporated, Wayzata, MN |

Example 1

The following chemical transesterification method was carried out to make Samples 405-3, 405D, 405E, 405F, 1120-1 and 607-1 in the Figures. All fatty acids (including dimer) or oils as described in Table 2 were pre-melted and heated to 70° C. before adding to the reaction vessel. The melted fatty acids or oils were then added to the reaction vessel and a nitrogen sparge was started to keep the product from oxidizing during the reaction. Glycerin was then added and the agitator was turned on to mix the contents. A caustic catalyst was added (Potassium Hydroxide (KOH) or Calcium Hydroxide ($Ca(OH)_2$)) at 0.1% dosage. Once all ingredients were added and well mixed the temperature was increased to 200 to 250° C. Reaction temperatures were varied to determine the impact reaction times would have on product properties. The reaction temperature was maintained until an acid value of 1.5 or less was achieved. An acid, Phosphoric Acid (85% concentration), was added at 0.2% to neutralize the catalyst with a slight excess. The mixture was cooled to 70° C. and an acid activated bleach clay, B80, was added to the reaction at 2% and allowed to absorb the salts from the catalyst. The product was then filtered to remove the salts and clay mixture as well as other impurities.

Example 2

The following enzymatic transesterification method was carried out to make Sample 405 Lipo. All fatty acids or oils as described in Table 2 were pre-melted and heated to 70° C. before adding to the reaction vessel. The melted fatty acids or oils were then added to the reaction vessel and a nitrogen sparge was started to keep the product from oxidizing during the reaction. The glycerin was then added and the agitator was turned on to mix the contents. 2% of an enzymatic catalyst, Lipase Novozyme 435, was added to the reaction. A vacuum of 50 torr was pulled on the sample to remove any water as the reaction was taking place. A temperature of 70° C. was maintained until an acid value of 1.5 or lower was achieved. The enzymatic catalyst was filtered out using a Buchner funnel and filter paper.

TABLE 2

Formulation Table (%)

| | 405-3 | 405D | 405E | 405F | 405 Lipo | 1120-1 | 607-1 |
| --- | --- | --- | --- | --- | --- | --- | --- |
| Glycerin | 30 | 20 | 20 | 20 | 20 | 20 | 30 |
| Fatty acid dimer (T18 Dimer) | 15 | 17 | 17 | 0 | 15 | 30 | 18 |
| TRV 1655 (Fatty Acid) | 45 | 0 | 52 | 63 | 0 | 0 | 0 |
| TRC 110 (Coconut FA) | 10 | 11 | 11 | 7 | 20 | 0 | 0 |
| TRV 1895 (Fatty Acid) | 0 | 52 | 0 | 0 | 45 | 50 | 0 |
| Coconut Oil | 0 | 0 | 0 | 0 | 0 | 0 | 10 |
| Hydrogenated Soy | 0 | 0 | 0 | 0 | 0 | 0 | 42 |

TABLE 3

Fatty Acid Makeup (%)

| | C8 | C10 | C12 | C14 | C16 | C18:0 | C18:1 |
| --- | --- | --- | --- | --- | --- | --- | --- |
| TRV 1655 (Fatty Acid) | 0 | 0 | 0 | 0.5 | 53.2 | 46.3 | 0 |
| TRV 1895 (Fatty Acid) | 0 | 0 | 0 | 0.1 | 6.2 | 93.5 | 0.2 |
| TRC 110 (Coconut Fatty Acid) | 8.7 | 6.5 | 48 | 18 | 8.5 | 3 | 6.5 |

Table 2 provides the formulations of each test sample. All samples in Table 2, except 405F, have dimer present in the formulation and are contemplated by the wax composition described herein. Note that paraffin is not included in Table 2 but commercially available paraffin (meeting basic industry standard parameters) was included as a comparative example as well as S-130 which is partially hydrogenated soy wax. Table 3 shows the fatty acid makeup of the fatty acid components listed in 2 1.

Table 4 provides gel permeation chromatography (GPC) results for the wax compositions described herein. Table 5 provides the GPC method parameters. Distinguishable from other commercially available wax compositions is the combination of polymer, MAGs, DAGs, and TAGs caused by dimer crosslinking during the esterification/transesterification reaction.

TABLE 4

GPC Data

| | Peak A (%) | Peak B (%) | Peak C (%) | Peak D (%) |
| --- | --- | --- | --- | --- |
| 405-3 | 14.9 | 13.3 | 31.4 | 38.7 |
| 405D | 21.9 | 15.1 | 35.2 | 27.8 |
| 405E | 26.1 | 14.7 | 33.7 | 25.5 |
| 405F | 0.0 | 12.6 | 53.0 | 28.1 |
| 405 Lipo | 17.3 | 16.2 | 38.7 | 26.2 |
| 1120-1 | 38.0 | 16.4 | 23.9 | 21.6 |
| 607-1 | 14.1 | 14.8 | 29.2 | 40.0 |
| S-130 | 0.0 | 99.8 | 0.2 | 0.0 |

Peak A corresponds to the largest molecular weight components (corresponding to an Mw range of 922 to 2751), Peak A describes acylglyceride polymers. Peak B corresponds to the medium-large molecular weight components (corresponding to an Mw range of 582 to 891). Peak B describes a fraction which includes the triacylglyceride component but also includes other medium-large molecular weight components. Peak C corresponds to small molecular weight components (corresponding to an Mw range of 400 to 568). Peak C describes the diacylglyceride component. Peak D corresponds to the smallest molecular weight components (corresponding to an Mw range of 218 to 358). Peak D describes the monoacylglyceride component.

TABLE 5

GPC Method

| | |
|---|---|
| Instrument | Waters 510 pump and a 410 differential refractometer |
| Temperature | 35° C. |
| Eluent/solvent | THF |
| Sample [Conc] | ~2% |
| Flow rate | 1 mL/minute |
| Columns | Phenogel 5 micron, linear/mixed, Cat# 03B-2088-KO 300 × 7.8 mm Phenogel 5 micron columns (styrene-divinylbenzene copolymer): 1) 50 Angstroms, Cat# 00H-0441-K 2) 100 Angstroms, Cat# 00H-0442-K0 3) 1000 Angstroms, Cat# 00H-0444-K0 4) 10000 Angstroms, Cat# 00H-04445-K0 |
| Software | Waters Breeze |

Figure 2:
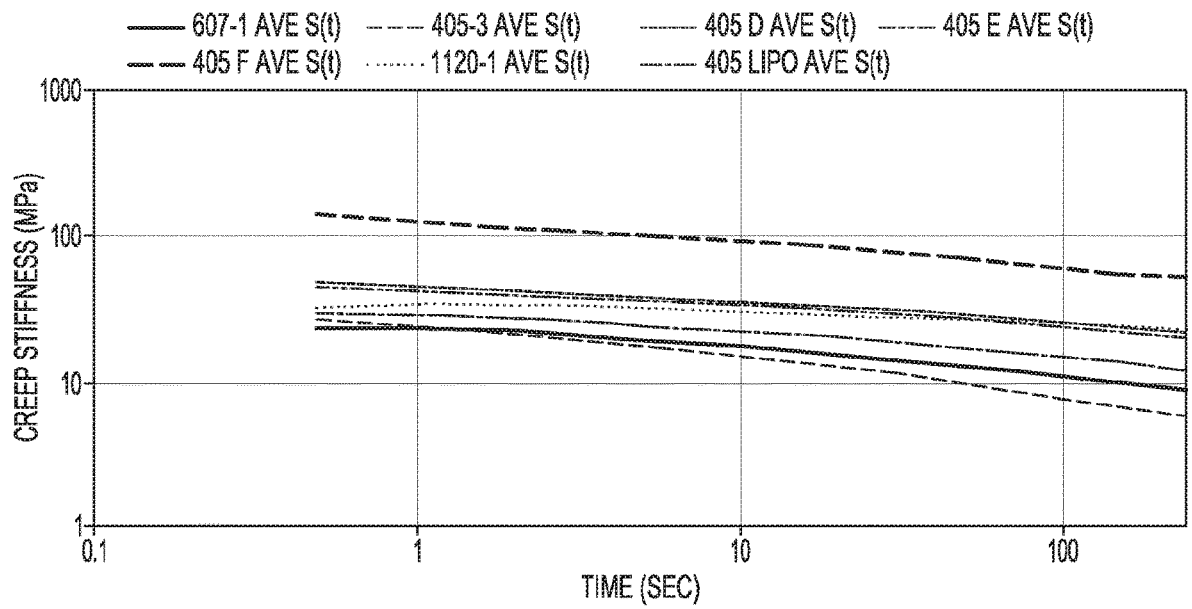
FIG. 2 shows a plot depicting the average creep stiffness (MPa) over time (seconds) for various vegetable wax compositions. The plot shows data for exemplified wax compositions and a comparative formulation that was prepared without the fatty acid dimer.

Use of the fatty acid dimer provides desirable flexibility across drop point of the wax composition that other commercially available wax compositions do not offer. Table 6, FIG. 1 and FIG. 2 provide average creep stiffness data (as determined by Standard Test Method for Determining The Flexural Creep Stiffness of Asphalt Binder Using the Bending Beam Rheometer, ASTM Method D 6648-08). Table 6 also provides drop point (° C.) as measured by ADCS Method Cc 18-80,

TABLE 6

| | 405-3 | 405-D | 405-E | 405-F | 405-Lipo | 1120-1 | 607-1 | S-130 | FRP Paraffin |
|---|---|---|---|---|---|---|---|---|---|
| Average Creep Stiffness | 9.38 | 27.20 | 25.43 | 67.44 | 16.41 | 27.37 | 12.13 | 170.15 | 142.20 |
| Drop Point of Wax (° C.) | 51.2 | 56.3 | 50.0 | 51.9 | 53.6 | 57.5 | 55.8 | 54.5 | 54.2 |

FIG. 1, specifically, compares the flexibility of wax compositions described herein to commercially available waxes, paraffin wax and partially hydrogenated soy wax (S-130). As illustrated in FIG. 1, paraffin and S-130 have much higher creep stiffness values indicating they are more rigid than the wax compositions described herein. FIG. 2, specifically, compares the flexibility of the vegetable based waxes described herein and highlights the desired wax flexibility in dimer crosslinked samples. Notably, 405-F, which does not contain the dimer crosslinking, does not achieve desired flexibility characteristics of the flexible wax compositions described herein, but is still more flexible than paraffin and the normal vegetable based waxes.

Example 3

Several wax compositions were heated and cooled while monitoring their interior temperature. The tested wax compositions were S-130 wax (a conventional, partially hydrogenated soy wax), a conventional paraffin wax, a blend of S-130 and the paraffin wax, and Example 405-3. Cooling was measured over a period of approximately six hours.

Figure 3:
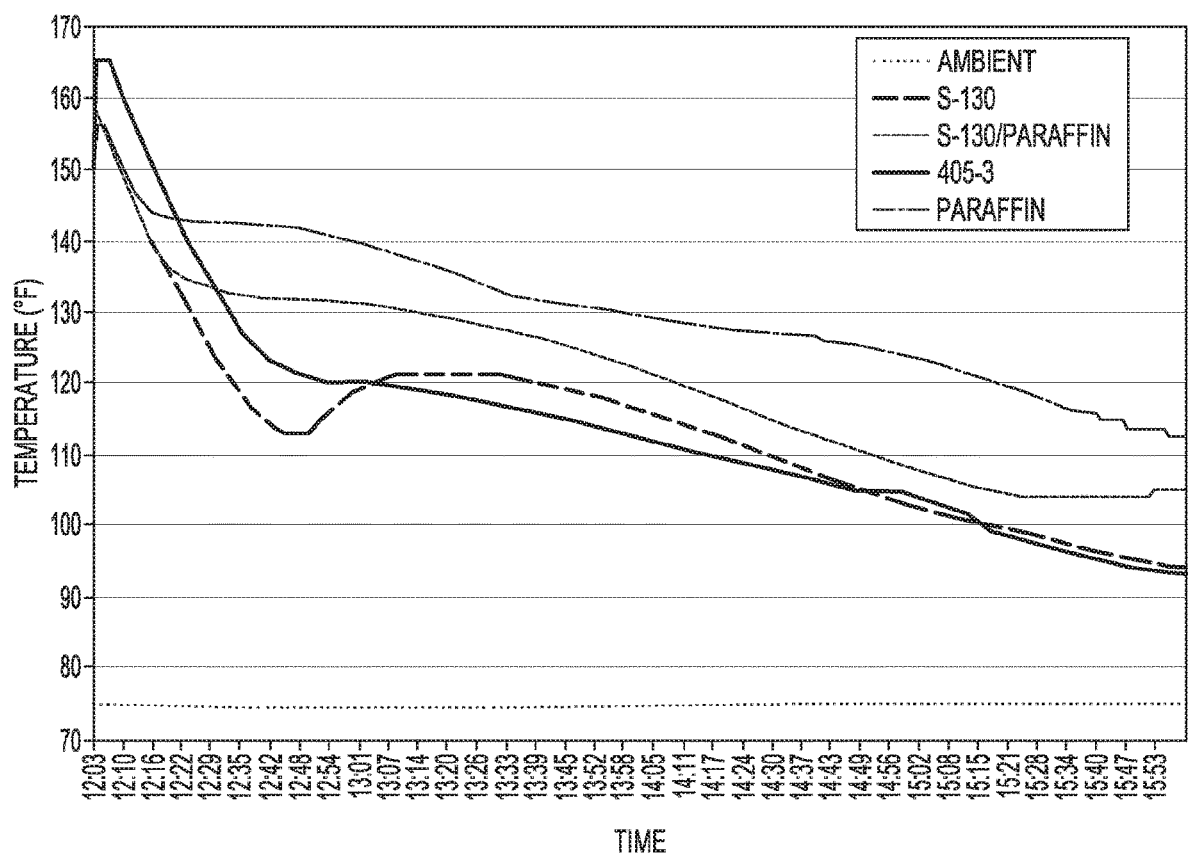
FIG. 3 shows a plot depicting the interior temperature (° F.) of various wax compositions as they cool over a period of approximately six hours. The ambient air temperature is also plotted.

As shown in FIG. 3, the conventional soy wax has a fast rate of initial cooling but then shows a significant temperature increase after about 45 minutes of cooling. The conventional paraffin wax shows the slowest rate of cooling. The blend of conventional soy wax and conventional paraffin wax shows a slow rate of cooling but also shows a cooling rate which flattens during a period from 30 minutes to 3 hours. In contrast, Example 405-3 shows a fast rate of cooling having a rate comparable to S-130 wax, but it does not suffer from a period of increasing temperature exhibited by the S-130 wax.

The temperature spike generated by the conventional soy wax disrupts and adversely effects the cooling process. Moreover, the appearance of the temperature increase may be due to heats of formation of the type of internal crystal structure, which could render wax susceptible to cracking. In contrast, the wax according to the present disclosure does not show any temperature increase. Without being limited to theory, one possible explanation for the above-discussed improvements, e.g., resistance to cracking, could be because the crystal structure of the wax is broken-up, thus leading the crystals to align in a random pattern rather than a rigid pattern upon cooling. It is believed that this differing internal structure allows the wax to bend and stretch, rather than break.

ENUMERATED EMBODIMENTS

The following exemplary embodiments are provided, the numbering of which is not to be construed as designating levels of importance:

Embodiment 1 provides a flexible wax composition, comprising about 10-45 wt % polymer, 20-45 wt % MAGs, 28-40 wt % DAGs, and 10-17 wt % TAGs.

Embodiment 2 provides the flexible wax composition of Embodiment 1 having an average creep stiffness of less than about 30 MPa.

Embodiment 3 provides the flexible wax composition of Embodiment 1 having an average creep stiffness of less than about 25 MPa.

Embodiment 4 provides the flexible wax composition of Embodiment 1 having an average creep stiffness of less than about 20 MPa.

Embodiment 5 provides the flexible wax composition of Embodiment 1 having an average creep stiffness of less than about 15 MPa.

Embodiment 6 provides the flexible wax composition of Embodiment 1 having an average creep stiffness of less than about 10 MPa.

Embodiment 7 provides the flexible wax composition of any one of Embodiments 1-6 having a drop point ranging from about 50-60° C.

Embodiment 8 provides the flexible wax composition of any one of Embodiments 1-7, wherein the composition is derived from a natural oil or natural oil derivative.

Embodiment 9 provides use of the flexible wax composition of any one of Embodiments 1-8 in candies.

Embodiment 10 provides the use of the flexible wax composition of any one of Embodiments 1-8 in paper coatings, box coatings, fruit coatings, broadsizing for OSB, tire and rubber, polyvinyl chloride (PVC) piping, crayons, and personal care.

Embodiment 11 provides a method of making a flexible wax composition, comprising:

mixing fatty acid and/or oil, a dimer, and glycerin to form a reaction mixture:

adding a caustic or enzymatic catalyst to facilitate a transesterification reaction until the reaction achieves an acid value of less than 1.5 to obtain a flexible wax composition comprising about 10-45 wt % polymer, 20-45 wt % MAGs, 28-40 wt % DAGs, and 10-17 wt % TAGS.

Embodiment 12 provides the method of Embodiment 11, wherein the flexible wax composition has an average creep stiffness of less than about 30 MPa.

Embodiment 13 provides the method of Embodiment 11, wherein the flexible wax composition has an average creep stiffness of less than about 25 MPa.

Embodiment 14 provides the method of Embodiment 11, wherein the flexible wax composition has an average creep stiffness of less than about 20 MPa.

Embodiment 15 provides the method of Embodiment 11, wherein the flexible wax composition has an average creep stiffness of less than about 15 MPa.

Embodiment 16 provides the method of Embodiment 11, wherein the flexible wax composition has an average creep stiffness of less than about 10 MPa.

Embodiment 17 provides the method of any one of Embodiments 11-16, wherein the flexible wax composition has a drop point ranging from about 50-60° C.

Embodiment 18 provides the method of any one of Embodiments 11-17, wherein the flexible wax composition is derived from a natural oil or natural oil derivative.

Embodiment 19 provides a flexible wax composition, comprising:

about 40 wt % to about 75 wt % monoacylglycerides and diacylglycerides having a weight average molecular weight of about 200 Da to about 580 Da, and at least 10 wt % acylglycerides having a weight average molecular weight (Mw) of about 900 Da to about 3000 Da.

Embodiment 20 provides a flexible wax composition, comprising:

about 20 wt % to about 45 wt % monoacylglycerides,
about 28 wt % to about 40 wt % diacylglycerides, and
at least 10 wt % acylglycerides having a weight average molecular weight (Mw) of about 900 Da to about 3000 Da.

Embodiment 21 provides a flexible wax composition, comprising:

about 20 wt % to about 45 wt % monoacylglycerides,
about 28 wt % to about 40 wt % diacylglycerides, and
about 10 wt % to about 45 wt % acylglyceride polymers,
wherein the acylglyceride polymers are compounds containing one or more dimerized fatty, acid residue and a plurality of glycerol moieties.

Embodiment 22 provides the flexible wax composition of Embodiment 21, wherein the dimerized fatty acid residue has the structure:

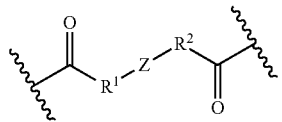

wherein R1 and R2 are each independently a divalent C7-C21 aliphatic group and Z is a bond or an oxygen atom.

Embodiment 23 provides the flexible wax composition of Embodiment 21 or 22, wherein $R^1$ and $R^2$ are each a divalent C18 aliphatic group and Z is a bond.

Embodiment 24 provides the flexible wax composition of any one of Embodiments 19-23, comprising about 1 wt % to about 17 wt % triacylglycerides.

Embodiment 25 provides the flexible wax composition of any one of Embodiments 19-24, wherein about 40 wt % to about 75 wt % of the composition is monoacylglycerides and diacylglycerides.

Embodiment 26 provides the flexible wax composition of any one of Embodiments 19-25, comprising less than about 2 wt % free fatty acids and free glycerin.

Embodiment 27 provides the flexible wax composition of any one of Embodiments 19-26, wherein about 20 wt % to about 45 wt % of the composition is acylglycerides having a weight average molecular weight (Mw) of about 200 Da to about 380 Da.

Embodiment 28 provides the flexible wax composition of any one of Embodiments 19-27, wherein about 28 wt % to about 40 wt % of the composition is acylglycerides having a weight average molecular weight (Mw) of about 380 Da to about 580 Da.

Embodiment 29 provides the flexible wax composition of any one of Embodiments 19-28, wherein about 10 wt % to about 17 wt % of the composition is acylglycerides having a weight average molecular weight (Mw) of about 580 Da to about 900 Da.

Embodiment 30 provides the flexible wax composition of any one of Embodiments 19-29, wherein about 10 wt % to about 45 wt % of the composition is acylglycerides having a weight average molecular weight (Mw) of 900 Da to about 3000 Da.

Embodiment 31 provides the flexible wax composition of any one of Embodiments 19-30, wherein at least 20 wt % of the composition is acylglycerides having a weight average molecular weight (Mw) of about 580 Da to about 3000 Da.

Embodiment 32 provides the flexible wax composition of any one of Embodiments 19-31, wherein at least 40 wt % of the composition is soybean oil.

Embodiment 33 provides the flexible wax composition of any one of Embodiments 19-32 having a drop point ranging from about 50-60° C.

Embodiment 34 provides the flexible wax composition of any one of Embodiments 19-33, which is a natural oil-based wax.

Embodiment 35 provides the flexible wax composition of any one of Embodiments 19-34 having an average creep stiffness of less than about 30 MPa.

Embodiment 36 provides the flexible wax composition of any one of Embodiments 19-34 having an average creep stiffness of less than about 25 MPa.

Embodiment 37 provides the flexible wax composition of any one of Embodiments 19-34 having an average creep stiffness of less than about 20 MPa.

Embodiment 38 provides the flexible wax composition of any one of Embodiments 19-34 having an average creep stiffness of less than about 15 MPa.

Embodiment 39 provides the flexible wax composition of any one of Embodiments 19-34 having an average creep stiffness of less than about 10 MPa.

Embodiment 40 provides use of the flexible wax composition of any one of Embodiments 1-39 in candles.

Embodiment 41 provides use of the flexible wax composition of any one of Embodiments 1-39 in paper coatings, box coatings, fruit coatings, broadsizing for OSB, tire and rubber, polyvinyl chloride (PVC) piping, crayons, and personal care.

Embodiment 42 provides a method of making the flexible wax composition of any one of Embodiments 1-39 comprising:
mixing fatty acid and/or oil, a fatty acid dimer, and glycerin to form a reaction mixture;
adding a caustic catalyst or an enzymatic catalyst that facilitates esterification and transesterification and permitting reaction proceed until the mixture achieves an acid value of less than 1.5 to obtain a flexible wax composition.

Embodiment 43 provides a method of making the flexible wax composition comprising:
mixing fatty acid and/or oil, a fatty acid dimer, and glycerin to form a reaction mixture;
adding a caustic catalyst or an enzymatic catalyst that facilitates esterification and transesterification and permitting reaction proceed until the mixture achieves an acid value of less than 1.5 to obtain a flexible wax composition.

Embodiment 44 provides the method of Embodiment 42 or 43, comprising mixing one or more fatty acid and one or more oil to form the reaction mixture.

Embodiment 45 provides the method of any one of Embodiments 42-44, wherein the fatty acid dimer has the structure:

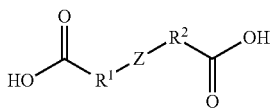

wherein R1 and R2 are each independently a divalent C7-C21 aliphatic group and Z is a bond or an oxygen atom.

Embodiment 46 provides the method of any one of Embodiments 42-45, wherein the catalyst is Lipase Novozyme 435, Potassium hydroxide (KOH) or Calcium Hydroxide (Ca(OH)$_2$.

Embodiment 47 provides the method of any one of Embodiments 42-46, wherein the fatty acid is a C8 free fatty acid, C10 free fatty acid, C12 free fatty acid, C14 free fatty acid. C16 free fatty acid, C18:0 free fatty acid, C18:1 free fatty acid, or a free fatty acid derived from canola oil, rapeseed oil, coconut oil, corn oil, cottonseed oil, olive oil, palm oil, peanut oil, safflower oil, sesame oil, soybean oil, sunflower oil, linseed oil, palm kernel oil, tong oil, Jatropha oil, mustard oil, camelina oil, pennycress oil, hemp oil, algal oil, castor oil, lard, tallow, poultry fat, yellow grease or fish oil, or a mixture thereof.

Embodiment 48 provides the method of any one of Embodiments 42-47, wherein the oil is canola oil, rapeseed oil, coconut oil, corn oil, cottonseed oil, olive oil, palm oil, peanut oil, safflower oil, sesame oil, soybean oil, sunflower oil, linseed oil, palm kernel oil, tong oil, jatropha oil, mustard oil, camelina oil, pennycress oil, hemp oil, algal oil, castor oil, lard, tallow, poultry fat, yellow grease, fish oil, or a mixture thereof.

Embodiment 49 provides the method of any one of Embodiments 42-48, wherein the oil is soybean oil.

Embodiment 50 provides a candle prepared from the flexible wax composition of any one of Embodiments 1-8 and 19-41 or prepared via the method of any one of Embodiments 11-18 and 42-49.

Embodiment 51 provides the composition, method or use of any combination of Embodiments 1-50 optionally configured such that all elements or options recited are available to use or select from.

The invention claimed is:

1. A flexible wax composition, comprising:
about 20 wt. % to about 45 wt. % monoacylglycerides,
about 28 wt. % to about 40 wt. % diacylglycerides, and
about 10 wt. % to
about 45 wt. % acylglyceride polymers, wherein the acylglyceride polymers are compounds containing one or more dimerized fatty acid residue and a plurality of glycerol moieties;
wherein the flexible wax composition has an average creep stiffness of less than about 30 M Pa.

2. The flexible wax composition of claim 1, wherein the one or more dimerized fatty acid residues have the structure:

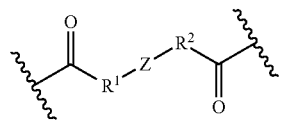

wherein $R^1$ and $R^2$ are each independently a divalent C7-C21 aliphatic group and Z is a bond or an oxygen atom.

3. The flexible wax composition of claim 2, wherein $R^1$ and $R^2$ are each a divalent C18 aliphatic group and Z is a bond.

4. The flexible wax composition of claim 1, comprising about 1 wt % to about 17 wt % triacylglycerides.

5. The flexible wax composition of claim 1, wherein about 48 40 wt % to about 75 wt % of the composition is monoacylglycerides and diacylglycerides.

6. The flexible wax composition of claim 1, comprising less than about 2 wt % free fatty acids and free glycerin.

7. The flexible wax composition of claim 1, wherein about 20 wt % to about 45 wt % of the composition is acylglycerides having a weight average molecular weight of about 200 Da to about 380 Da.

8. The flexible wax composition of claim 1, wherein about 28 wt % to about 40 wt % of the composition is acylglycerides having a weight average molecular weight of about 380 Da to about 580 Da.

9. The flexible wax composition of claim 1, wherein about 10 wt % to about 17 wt % of the composition is acylglycerides having a weight average molecular weight of about 580 Da to about 900 Da.

10. The flexible wax composition of claim 1, wherein about 10 wt % to about 45 wt % of the composition is acylglycerides having a weight average molecular weight of 900 Da to about 3000 Da.

11. The flexible wax composition of claim 1, wherein at least 20 wt % of the composition is acylglycerides having a weight average molecular weight of about 580 Da to about 3000 Da.

12. The flexible wax composition of claim 1, wherein at least 40 wt % of the composition is soybean oil.

13. The flexible wax composition of claim 1 having a drop point ranging from about 50-60° C.

14. The flexible wax composition of claim 1, which is a natural oil-based wax.

15. The flexible wax composition of claim 1 having an average creep stiffness of less than about 15 MPa.

16. A candle comprising the flexible wax composition of claim 1.

17. A paper coating, box coating, fruit coating oriented strand board, tire, rubber, polyvinyl chloride piping, crayon, or personal care product comprising the flexible wax composition of claim 1.

18. A method of making a flexible wax composition, comprising:
mixing fatty acid and/or oil, a fatty acid dimer, and glycerin to form a mixture; and
adding a caustic or enzymatic catalyst to the mixture to facilitate esterification and transesterification reactions until the mixture achieves an acid value of less than 1.5, so as to obtain a flexible wax composition, the flexible wax composition comprising
about 20 wt % to about 45 wt % monoacylglycerides,
about 28 wt % to about 40 wt % diacylglycerides, and
about 10 wt % to about 45 wt % acylglyceride polymers, wherein the acylglyceride polymers are compounds containing the one or more dimerized fatty acid residues and a plurality of glycerol moieties;
wherein the flexible wax composition has an average creep stiffness of less than about 30 Mpa.

19. A flexible wax composition, comprising:
about 20 wt % to about 45 wt % monoacylglycerides,
about 28 wt % to about 40 wt % diacylglycerides, and
about 10 wt % to about 45 wt % acylglyceride polymers;
wherein
the acylglyceride polymers are compounds containing the one or more dimerized fatty acid residues and a plurality of glycerol moieties,
the dimerized fatty acid residues have the structure:

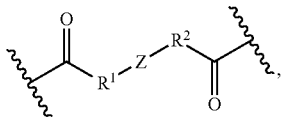

and
$R^1$ and $R^2$ are each a divalent C18 aliphatic group and Z is a bond.

* * * * *